US010238870B2

(12) United States Patent
Pilly et al.

(10) Patent No.: US 10,238,870 B2
(45) Date of Patent: Mar. 26, 2019

(54) TRANSCRANIAL CONTROL OF PROCEDURAL MEMORY RECONSOLIDATION FOR SKILL ACQUISITION

(71) Applicant: HRL Laboratories, LLC, Malibu, CA (US)

(72) Inventors: Praveen K. Pilly, West Hills, CA (US); Michael D. Howard, Westlake Village, CA (US); Rajan Bhattacharyya, Sherman Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 0 days.

(21) Appl. No.: 15/336,181

(22) Filed: Oct. 27, 2016

(65) Prior Publication Data

US 2017/0312519 A1  Nov. 2, 2017

Related U.S. Application Data

(60) Provisional application No. 62/247,106, filed on Oct. 27, 2015.

(51) Int. Cl.
| | |
|---|---|
| *A61N 1/36* | (2006.01) |
| *A61B 5/0482* | (2006.01) |
| *A61B 5/0476* | (2006.01) |
| *A61B 5/00* | (2006.01) |
| *A61N 1/04* | (2006.01) |
| *G09B 19/00* | (2006.01) |

(52) U.S. Cl.
CPC ........ *A61N 1/36025* (2013.01); *A61B 5/0476* (2013.01); *A61B 5/0482* (2013.01); *A61B 5/4836* (2013.01); *A61N 1/0456* (2013.01); *G09B 19/003* (2013.01)

(58) Field of Classification Search
CPC .............. A61N 1/36025; A61N 1/0456; G09B 19/0003; A61B 5/0476; A61B 5/4836
See application file for complete search history.

(56) References Cited

U.S. PATENT DOCUMENTS

| 8,718,778 B2 | 5/2014 | Bikson et al. |
| 9,116,835 B1 | 8/2015 | Smyth |

(Continued)

FOREIGN PATENT DOCUMENTS

JP    2010-501479    1/2010

OTHER PUBLICATIONS

International Search Report of the International Searching Authority for PCT/US2016/059129; dated Feb. 3, 2017.

(Continued)

*Primary Examiner* — Joseph M Dietrich
(74) *Attorney, Agent, or Firm* — Tope-McKay & Associates (57) ABSTRACT

Described is a system for the therapeutic modification of human behavior and, more specifically, a system for the transcranial control of procedural memory reconsolidation for the purposes of enhanced skill acquisition. During operation the system records a practice pattern. The practice pattern is a recording of a sensed brain activity from a sensor array when a subject is performing a skill. The practice pattern is converted to brain activity voxels and stored as both an uncompressed practice pattern and a compressed practice pattern.

24 Claims, 6 Drawing Sheets

(56) References Cited

U.S. PATENT DOCUMENTS

| | | | |
|---|---|---|---|
| 9,370,658 B2 | 6/2016 | Neuvonen | |
| 2006/0239482 A1* | 10/2006 | Hatoum | A61N 1/025 381/312 |
| 2008/0004660 A1 | 1/2008 | Assaf et al. | |
| 2009/0319002 A1 | 12/2009 | Simon | |
| 2012/0046531 A1 | 2/2012 | Hua | |
| 2012/0156659 A1 | 6/2012 | Yun | |
| 2012/0245653 A1 | 9/2012 | Bikson et al. | |
| 2012/0265261 A1 | 10/2012 | Bikson | |
| 2014/0057232 A1 | 2/2014 | Wetmore et al. | |
| 2015/0025590 A1 | 1/2015 | Cheng | |
| 2015/0164361 A1 | 6/2015 | Lunner | |
| 2016/0228702 A1 | 8/2016 | Kempe | |

OTHER PUBLICATIONS

The Written Opinion of the International Searching Authority for PCT/US2016/059129; dated Feb. 3, 2017.

Notification of Transmittal of International Search Report and the Written Opinion of the International Searching Authority for PCT/US2016/059129; dated Feb. 3, 2017.

Censor N, Dayan E, Cohen LG. Cortico-subcortical neuronal circuitry associated with reconsolidation of human procedural memories. Cortex. (2014);58: pp. 281-288.

Cousins JN, El-Deredy W, Parkes LM, Hennies N, Lewis PA. Cued Memory Reactivation during Slow-Wave Sleep Promotes Explicit Knowledge of a Motor Sequence. J. Neurosci. (2014);34: pp. 15870-15876.

Stepnowsky C., et al. Scoring accuracy of automated sleep staging from a bipolar electroocular recording compared to manual scoring by multiple raters, Sleep Medicine 14 (2013) pp. 1199-1207, found at http://dx.doi.org/10.1016/j.sleep.2013.04.022.

McNamara CG, Tejero-Cantero A, Trouche S, Campo-Urriza N, Dupret D. Dopaminergic neurons promote hippocampal reactivation and spatial memory persistence. Nat Neurosci. 2014;17: pp. 1658-1660.

Marshall L, Helgadóttir H, Mölle M, Born J. Boosting slow oscillations during sleep potentiates memory. Nature. 2006;444: pp. 610-613.

Javadi AH, Walsh V. Transcranial direct current stimulation (IDCS) of the left dorsolateral prefrontal cortex modulates declarative memory. Brain Stimulat. 2012;5: pp. 231-241.

Rasch B, Büchel C, Gais S, Born J. Odor cues during slow-wave sleep prompt declarative memory consolidation. Science. 2007;315: pp. 1426-1429.

Rudoy JD, Voss JL, Westerberg CE, Paller KA. Strengthening Individual Memories by Reactivating Them During Sleep. Science. 2009;326: p. 1079.

Bendor D, Wilson MA. Biasing the content of hippocampal replay during sleep. Nat. Neurosci. 2012;15: pp. 1439-1444.

Euston DR, Gruber AJ, McNaughton BL. The role of medial prefrontal cortex in memory and decision making. Neuron. 2012;76: pp. 1057-1070.

Ji D, Wilson MA. Coordinated memory replay in the visual cortex and hippocampus during sleep. Nat. Neurosci. 2007;10: pp. 100-107.

Abeyratne UR, Swarnkar V, Rathnayake SI, Hukins C. Sleep-stage and event dependency of brain asynchrony as manifested through surface EEG. Conf. Proc. Annu. Int. Conf. IEEE Eng. Med. Biol. Soc. IEEE Eng. Med. Biol. Soc. Conf. 2007;2007: pp. 709-712.

Salmi T, Brander PE. Computer assisted detection of REM and non-REM sleep for analysis of nocturnal hypoxaemia in patients with ventilatory impairment. Int. J. Clin. Monit. Comput. 1994;11: pp. 63-70.

Euston et al. Fast-Forward Playback of Recent Memory Sequences in Prefrontal Cortex During Sleep. Science. Nov. 2007; 318 (5853): pp. 1147-1150.

The SenseWear armband as a Sleep Detection Device [Internet]. [cited Nov. 23, 2014]. pp. 1-9. Available from: http://www.bodymedia.com/Professionals/Whitepapers/The-SenseWear-armband-as-a-Sleep-Detection-Device?whence=.

Ruffini et al., Optimization of multifocal transcranial current stimulation for weighted cortical pattern targeting from realistic modeling of electric fields, Neuroimage, 89:216-25, 2014.

Rissman and Wagner, "Distributed Representations in Memory: Insights from Functional Brain Imaging," Annual Rev Psychol, 63: 101-128,2012.

Rolls, "The Mechanisms for Pattern Completion and Pattern Separation in the Hippocampus," Frontiers in Systems Neuroscience, 7: 74, 2013.

McHugh et al, "Dentate Gyms NMDA Receptors Mediate Rapid Pattern Separation in the Hippocampal Network," Science, 317(5834): 94-99, 2007.

Michael Schirner, et al., "An automated pipeline for constructing personalized virtual brains from multimodal neuroimaging data," NeuroImage, vol. 117, Aug. 15, 2015, pp. 343-357.

Krause, M. R., Zanos, T. P., Csorba, B. A., Pilly, P. K., Choe, J., Phillips, M. E., Datta, A., and Pack, C. C. (2017). Transcranial direct current stimulation facilitates assocative learning and alters functional connectivity in the primate brain. Current Buology, 27(3), pp. 3086-3096.

Offie Action 1 for U.S. Appl. No. 15/277,922, dated Dec. 13, 2016.

Tremblay, Sara, et al. "The Uncertain Outcome of Prefrontal TDCS." Brain Stimulation 7.6 (2014): 773-83. Web.

Segrace, R.A. et al. "Concurrent Cognitive Control Training Augments the Antidepressant Efficacy of TDCS: A Pilot Study." Brain Stimulation 7.2 (2014): 325-31. Web.

Castano-Candamil, Ssebastian et al. "Solving the EEG Inverse Problem Based on Space-Time-Frequency Structured Sparsity Constraints." Neuroimage 118 (2015) 598-612. Web.

Marshall, L. "Transcranial Direct Current Stimulation during Sleep Improves Declarative Memory." Journal of Neuroscience 24.44 (2004): 9985-992. Web.

Javadi, Amir Homayoun, and Paul Cheng. "Transcranial Direct Current Stimulation (tDCS) Enhances Reconsolidation of Long-Term Memory." Brain Stimulation 6.4 (2013): 668-74. Web.

Sahlem, Gregory L, et al. "Oscillating Square Wave Transcranial Direct Current Stimulation (tDCS) Delivered During Slow Wave Sleep Does Not Improve Declarative Memory More Than Sham: A Randomized Sham Controlled Crossover Study." Brain Stimulation 8.3 (2015): 528-34. Web.

Barham, Michael P., Peter G. Enticott, Russell Conduit, and Jarrad A.g. Lum. "Transcranial Electrical Stimulation during Sleep Enhances Declarative (but Not Procedural) Memory Consolidation: Evidence from a Meta-analysis."Neuroscience & Biobehavioral Reviews 63 (2016): 65-77. Web.

Eggert, Torsten, Hans Dorn, Cornelia Sauter, Michael A. Nitsche, Malek Bajbouj, and Heidi Danker-Hopfe. "No Effects of Slow Oscillatory Transcranial Direct Current Stimulation (tDCS) on Sleep-Dependent Memory Consolidation in Healthy Elderly Subjects." Brain Stimulation 6.6 (2013): 938-45. Web.

Westerberg, Carmen E., Susan M. Florczak, Sandra Weintraub, M.-Marsel Mesulam, Lisa Marshall, Phyllis C. Zee, and Ken A. Paller. "Memory Improvement via Slow-oscillatory Stimulation during Sleep in Older Adults." Neurobiology of Aging 36.9 (2015): 2577-586. Web.

Response to Office Action 1 for U.S. Appl. No. 15/227,922, dated Mar. 13, 2017.

Office Action 2 for U.S. Appl. No. 15/227,922, dated Apr. 24, 2017.

Response to Office Action 2 for U.S. Appl. No. 15/227,922, dated Aug. 24, 2017.

Office Action 3 for U.S. Appl. No. 15/227,922, dated Sep. 29, 2017.

Response to Office Action 3 for U.S. Appl. No. 15/227,922, dated Jan. 29, 2018.

Grech, R., Cassar, T., Muscat, J., Camilleri, K.P., Fabri, S.G., Zervakis, M., Xanthopoulos, R, Sakkalis, V. and Vanrumste, B., 2008. Review on solving the inverse problem in EEG source analysis. Journal of neuroengineering and rehabilitation, 5(1), pp. 1-33.

(56) References Cited

OTHER PUBLICATIONS

Tucker DM. Spatial sampling of head electrical fields: the geodesic sensor net. Electroencephalogr. Clin. Neurophysiol, 87: pp. 154-63, 1993.
Michel C., Murray MM. Towards the utilization of EEG as a brain imaging tool, NeuroImage 61 (2012), pp. 371-385.
Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage, 30: pp. 813-826, 2006.
Dmochowski JP, Datta A, Bikson M, Su Y, Parra LC. Optimized multi-electrode stimulation increases focality and intensity at target. J. Neural Eng., 8:046011, 2011, pp. 1-16.
Jones DK and Leemans A, "Diffusion Tensor Imaging", Methods in Molecular Biology 711: pp. 127-144, 2011.
Ramírez, Rey R., and Scott Makeig. "Neuroelectromagnetic source imaging of spatiotemporal brain dynamical patterns using frequency-domain independent vector analysis (IVA) and geodesic sparse Bayesian learning (gSBL)." In Proceedings of the 13th Annual Meeting of the Organization for Human Brain Mapping, Chicago, IL. 2007.
Nader K, Schafe GE, Le Doux JE. Fear memories require protein synthesis in the amygdala for reconsolidation after retrieval. Nature. 2000; 406: pp. 722-726.
Dudai Y. The neurobiology of consolidations, or, how stable is the engram? Annu. Rev. Psychol. 2004; 55: pp. 51-86.
Squire LR, Alvarez P. Retrograde amnesia and memory consolidation: a neurobiological perspective. Curr. Opin. Neurobiol. 1995; 5: pp. 169-177.
Foa EB. Social anxiety disorder treatments: psychosocial therapies. J. Clin. Psychiatry. 2006; 67 Suppl 12: pp. 27-30.
Seidler GH, Wagner FE. Comparing the efficacy of EMDR and trauma-focused cognitive-behavioral therapy in the treatment of PTSD: a meta-analytic study. Psychol. Med. 2006; 36: pp. 1515-1522.
Bustos SG, Maldonado H, Molina VA. Midazolam disrupts fear memory reconsolidation. Neuroscience. 2006; 139: pp. 831-842.
Sandrini M, Censor N, Mishoe J, Cohen LG. Causal Role of Prefrontal Cortex in Strengthening of Episodic Memories through Reconsolidation. Curr. Biol. 2013; 23: pp. 2181-2184.
Soterix Medical Website. High Definition-transcranial Direct Current Stimulation (HD-tDCS) [Internet]. Available from: http://soterixmedical.com/hd-tdcs, downloaded Aug. 8, 2016, pp. 1-13.
Chan JCK, LaPaglia JA. Impairing existing declarative memory in humans by disrupting reconsolidation. Proc. Natl. Acad. Sci. 2013;110: pp. 9309-9313.
Brunet A, Orr SP, Tremblay J, Robertson K, Nader K, Pitman RK. Effect of post-retrieval propranolol on psychophysiologic responding during subsequent script-driven traumatic imagery in post-traumatic stress disorder. J. Psychiatr. Res. 2008;42: pp. 503-506.
Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage. 2006; 30: pp. 813-826.
Dmochowski JP, Datta A, Bikson M, Su Y, Parra LC. Optimized multi-electrode stimulation increases focality and intensity at target. J. Neural Eng. 2011; 8:pp. 046011-1-046011-16.
Edmund Rolls, "The mechanisms for pattern completion and pattern separation in the hippocampus," Front Syst Neurosci. Oct. 2013; vol. 7: Article 74, pp. 1-21.
Thomas J. McHugh, et al., "Dentate Gyrus NMDA Receptors Mediate Rapid Pattern Separation in the Hippocampal Network," Science, vol. 317, (Jul. 2007); pp. 94-99.
Jesse Rissman, et al., "Distributed representations in memory: Insights from functional brain imaging," Annu Rev Psychol. 2012 ; 63: pp. 101-128.
Giulio Ruffinia, et al., "Optimization of multifocal transcranial current stimulation for weighted cortical pattern targeting from realistic modeling of electric fields," Neuroimage. Apr. 1, 2014; 89: pp. 216-225.
Office Action 1 for U.S. Appl. No. 15/072,353 dated Oct. 19, 2016.
Tremblay, Sara, et al., "The uncertain outcome of prefrontal TDCS," Brain Stimulation 7.6 (2014): pp. 773-783. Web.
Segrave, R.A., et al., "Concurrent cognitive control training augments the anidepressant efficacy of TDCS: A pilot study," Brain Stimulation 7.2 (2014): pp. 325-331. Web.
Castano-Candamil, Sebastian, et al., "Solving the EEG inverse problem based on space-time-frequency structured sparsity constraints," Neuroimage 118 (2015), pp. 598-612. Web.
Response to Office Action 1 for U.S. Appl. No. 15/072,353, dated Feb. 17, 2017.
Office Action 2 for U.S. Appl. No. 15/072,353, dated Apr. 24, 2017.
"An automated pipeline for constructing personalized virtual brains from multimodal neuroimaging data," NeuroImage, vol. 117, Aug. 15, 2015, pp. 343-357.
Krause, M. R., Zanos, T. P., Csorba, B. A., Pilly, P. K., Choe, J., Phillips, M. E., Datta, A., and Pack, C. C. (2017). Transcranial direct current stimulation facilitates associative learning and alters functional connectivity in the primate brain. Current Biology, 27(3), pp. 3086-3096.
Response to Office Action 2 for U.S. Appl. No. 15/072,353, dated Aug. 22, 2017.
Office Action 3 for U.S. Appl. No. 15/072,353, dated Oct. 6, 2017.
Response to Office Action 3 for U.S. Appl. No. 15/072,353, dated Jan. 8, 2018.
Notice of International Preliminary Report on Patentability for PCT/US2016/059129; dated May 11, 2018.
International Preliminary Report on Patentability for PCT/US2016/059129; dated May 11, 2018.

* cited by examiner

TRANSCRANIAL CONTROL OF PROCEDURAL MEMORY RECONSOLIDATION FOR SKILL ACQUISITION

CROSS-REFERENCE TO RELATED APPLICATIONS

This is a non-provisional patent application of U.S. Provisional Application No. 62/147,106, filed on Oct. 27, 2015, the entirety of which is hereby incorporated by reference.

BACKGROUND OF INVENTION

(1) Field of Invention

The present invention relates to devices for the therapeutic modification of human behavior and, more specifically, to a procedural memory enhancement system for the transcranial control of procedural memory reconsolidation for the purposes of enhanced skill acquisition.

(2) Description of Related Art

Procedural skills are learned in the declarative memory system and then gradually transferred to procedural memory over time (See the List of Incorporated Literature References, Reference No. 1). As can be appreciated, it is desirable to enhance the speed and efficiency of this transfer, and eliminate "bad habits" (i.e., inappropriate procedural behaviors). Researchers have attempted to improve such procedural skills through a variety of techniques, including transcranial stimulation.

Within the field of potentially therapeutic devices for transcranial stimulation, Cousins et al. used "Targeted Memory reactivation" during sleep to improve a procedural skill (See Literature Reference No. 2). The method described therein, however, requires that a tone sequence be present during the skill learning. During sleep, the tone sequence can be replayed, and it was found that it can cue the memory of the skill, thereby improving learning of the skill. The disadvantages are that this requires that a unique tone sequence be played at the same time each procedural skill is learned, and replayed during sleep. There is no way to interfere with reconsolidation of inappropriate execution of the skill during waking state. Furthermore, it is necessary with the Cousins' approach for the user to implicitly learn the association of the tone sequence to the skill, which may require many repetitions, all of which should be done without error.

Thus, a continuing need exists for a procedural memory enhancement system for the transcranial control of procedural memory reconsolidation for the purposes of enhancing skill acquisition during both waking and sleep to proactively disrupt the reconsolidation of a bad execution of a skill memory during waking state to weaken it electrically, and also to rehearse the proper execution of the skill automatically and periodically during sleep.

SUMMARY OF INVENTION

A procedural memory enhancement system. In various embodiments, the system comprises one or more processors and a memory. The memory is a non-transitory computer-readable medium having executable instructions encoded thereon, such that upon execution of the instructions, the one or more processors perform several operations, including recording a practice pattern (the practice pattern being a recording of a sensed brain activity from a sensor array when performing a skill); and converting the practice pattern to brain activity voxels and storing the brain activity voxels as both an uncompressed practice pattern and a compressed practice pattern.

In another aspect, a stimulator array is included for applying a stimulus montage to a subject.

Further, in recording the practice pattern, the practice pattern is recorded when the skill is performed correctly (e.g., the notes to a song are played correctly, etc.).

Additionally, while a subject is awake and practicing the skill, the system is operable for determining a required stimulus montage that maximizes a difference between the uncompressed practice pattern and a current brain activity and transcranially applying the stimulus montage to a subject through a stimulator array during subsequent waking practice of the skill.

In yet another aspect, while a subject is awake and incorrectly practicing the skill (e.g., playing the musical notes to a song incorrectly), the system is operable for transcranially applying a stimulus montage corresponding to the uncompressed practice pattern to interfere with reconsolidation and break bad habits.

Further, the system is also operable for periodically while a subject is asleep, transcranially applying the compressed practice pattern as a stimulus montage to the subject through a stimulator array, thereby cueing memories of performance of the skill.

Additionally and responsive to user input, the system is operable for adjusting a compression level used to form the compressed practice pattern to adapt sleep training to the subject and thereby increase individual sleep training effectiveness.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to devices for the therapeutic modification of human behavior and, more specifically, to a procedural memory enhancement system for the transcranial control of procedural memory reconsolidation for the purposes of enhanced skill acquisition. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth it order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of incorporated literature references is provided. Next, a description of the various principal aspects of the present invention is provided. Subsequently, an introduction provides the reader with a general understanding of the present invention. Finally, specific details of various aspects of the present invention are provided to give an understanding of the specific aspects.

(1) List of Incorporated Literature References

The following references are cited throughout this application. For clarity and convenience, the references are listed herein as a central resource for the reader. The following references are hereby incorporated by reference as though fully set forth herein. The references are cited in the application by referring to the corresponding literature reference number, as follows:

1. Censor N, Dayan E, Cohen L G. Cortico-subcortical neuronal circuitry associated with reconsolidation of human procedural memories. Cortex. (2014); 58-281-8.
2. Cousins J N, El-Deredy W, Parkes L M, Hennies N, Lewis P A. Cued Memory Reactivation during Slow-Wave Sleep Promotes Explicit Knowledge of a Motor Sequence. J. Neurosci. (2014); 34:15870-6.
3. Euston D R, Gruber A J, McNaughton B L. The role of medial prefrontal cortex in memory and decision making. Neuron. (2012); 76:1057-70.
4. Ji D, Wilson M A. Coordinated memory replay in the visual cortex and hippocampus during sleep. Nat. Neurosci. (2007); 10:100-7.
5. Stepnowsky C., et al. Scoring accuracy of automated sleep staging from a bipolar electroocular recording compared to manual scoring by multiple raters. Sleep Med (2013), found at http://dx.doi.org/10.1016/j.sleep.2013.04.022.

(2) Principal Aspects

Various embodiments of the invention include three "principal" aspects. The first is a procedural memory enhancement system for the transcranial control of procedural memory reconsolidation for skill acquisition. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

Figure 1:
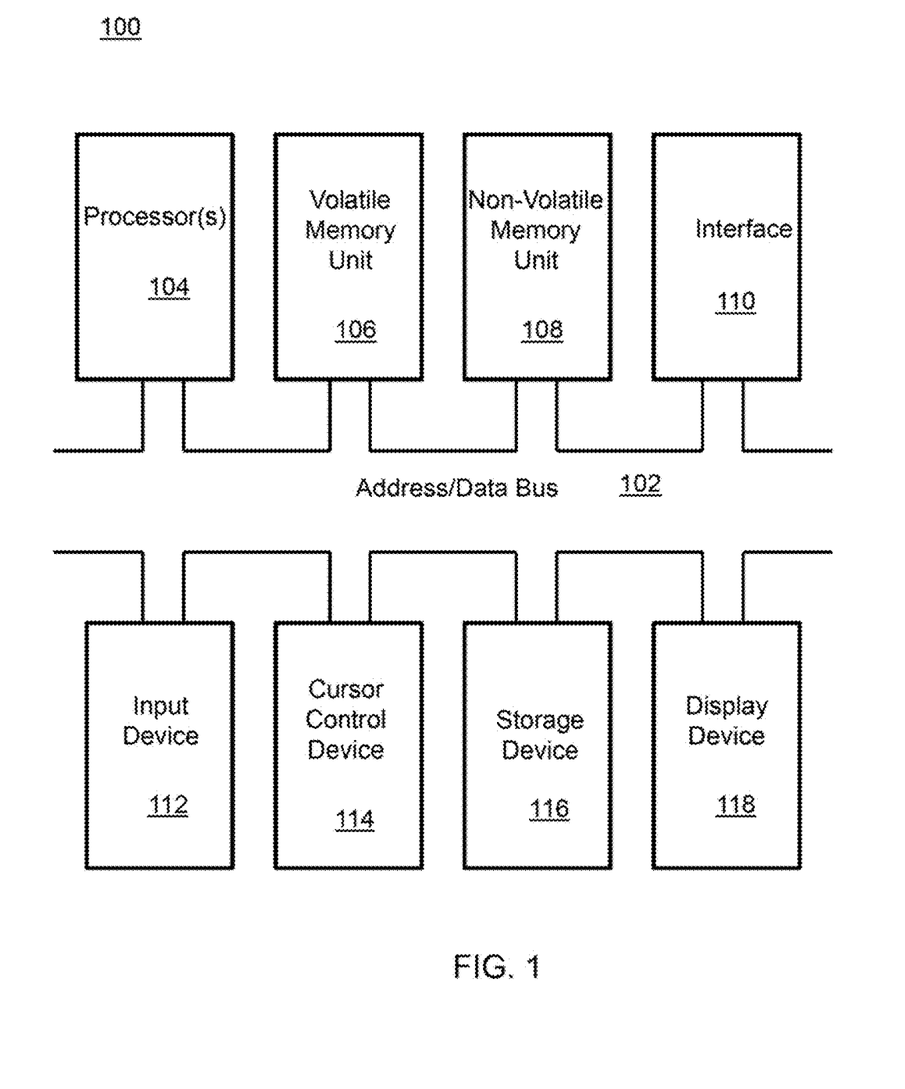
FIG. 1 is a block diagram depicting the components of a system according to some embodiments of the present disclosure.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
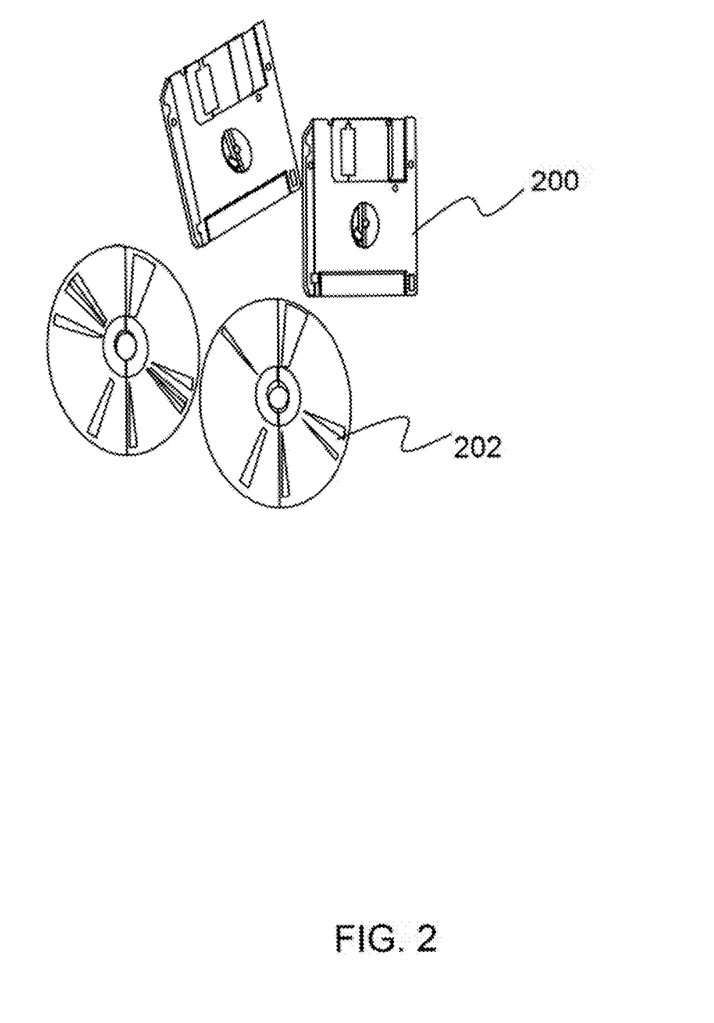
FIG. 2 is an illustration of a computer program product according to some embodiments of this disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) Introduction

Procedural skills are learned in the declarative memory system and then gradually transferred to procedural memory over time. Enhancing the speed and efficiency of this transfer, and eliminating "bad habits" (i.e., inappropriate procedural behaviors), is the focus of the present disclosure. In short, during the waking hours of a subject on which it is being used, the procedural memory enhancement system described herein records brain activity during proper execution of a skill. Subsequently, when there is a bad or improper execution, the system can be activated to disrupt reconsolidation by applying a stimulation pattern that roughly recreates the brain activity of the proper execution of the skill. The reconsolidation of bad habits can also be disrupted by transcranial cathodal stimulation, which decreases cell excitability, in cortical areas important for motor planning and execution (e.g., primary motor cortex (M1), supplementary motor area (SMA)). The system is also useful during sleep, to periodically recreate the brain state of good execution of the skill, thereby cueing a recall of the skill and speeding up transfer of the skill to the subject's procedural memory system.

While learning the skill (or practicing it deliberately and accurately), spatiotemporally distributed brain activity is recorded from sensors such as high-resolution EEG and fNIRS. This is called the "Practice pattern." Subsequently, either during waking hours or sleep, the practice pattern is applied using a transcranial stimulation cap, which sends low levels of high-definition transcranial current stimulation into the brain to recreate the practice pattern by affecting cell excitability across distributed brain areas. The treatment will feel like no more than a minor tingling sensation because it is low voltage (e.g., on the order of a small battery). This procedure for using transcranial electrical stimulation to enhance procedural skill learning and weaken bad habits is unique.

The targeted procedural memory enhancement system of the present disclosure will speed up acquisition of procedural skills, and also speed up correction of bad habits, without physical risk to the patient. When learning how to play an instrument, touch type on a keyboard, drive a car, serve in tennis, swim, or acquire other procedural skills, one is trained by instructions, rules, and advice. For example, a tennis serve requires a complex coordinated movement that orchestrates the drawing back of the racket, the tossing of the ball to a certain height, and a particular way of moving the torso as the racket swings overhead to hit the ball. At first this training takes the form of a set of rules in memory, and the student practices many times, possibly for years, to learn to perform it skillfully. The skillful practitioner no longer thinks about the details of the performance, but instead will focus on high-level goals like where in the opposing court to aim the ball, or what kind of spin to put on it. Thus, procedural memory is called "implicit" in contrast to the explicit nature of declarative memories.

A conspicuous problem with the formation of skills tied to procedural memory is that it is very common to fall into bad habits while learning. Accordingly, when the student takes lessons to try to improve such a skill, the teacher must help the student break these bad habits. Also, new skill acquisition can be slow due to interference from a habitual action; e.g., learning tennis by someone tuned to playing racquetball. The system of the present invention will record the brain activity during initial deliberative, focused learning or practice of the skill. It will use this pattern not only to disrupt reconsolidation of bad waking performances of the skill, but also to cue recall during sleep so as to increase the speed at which the explicit declarative memory is transferred to implicit procedural memory. Thus, the system of this disclosure can be employed to reduce practice required, and to break bad habits that interfere with good performance.

Notably, the procedural memory enhancement system according to this disclosure does not require pharmacological intervention (e.g., stimulants), which are systemic and can have undesirable side effects such as dependencies. The system could, however, be potentially useful in treating dependency issues that have physical manifestations.

Figure 3:
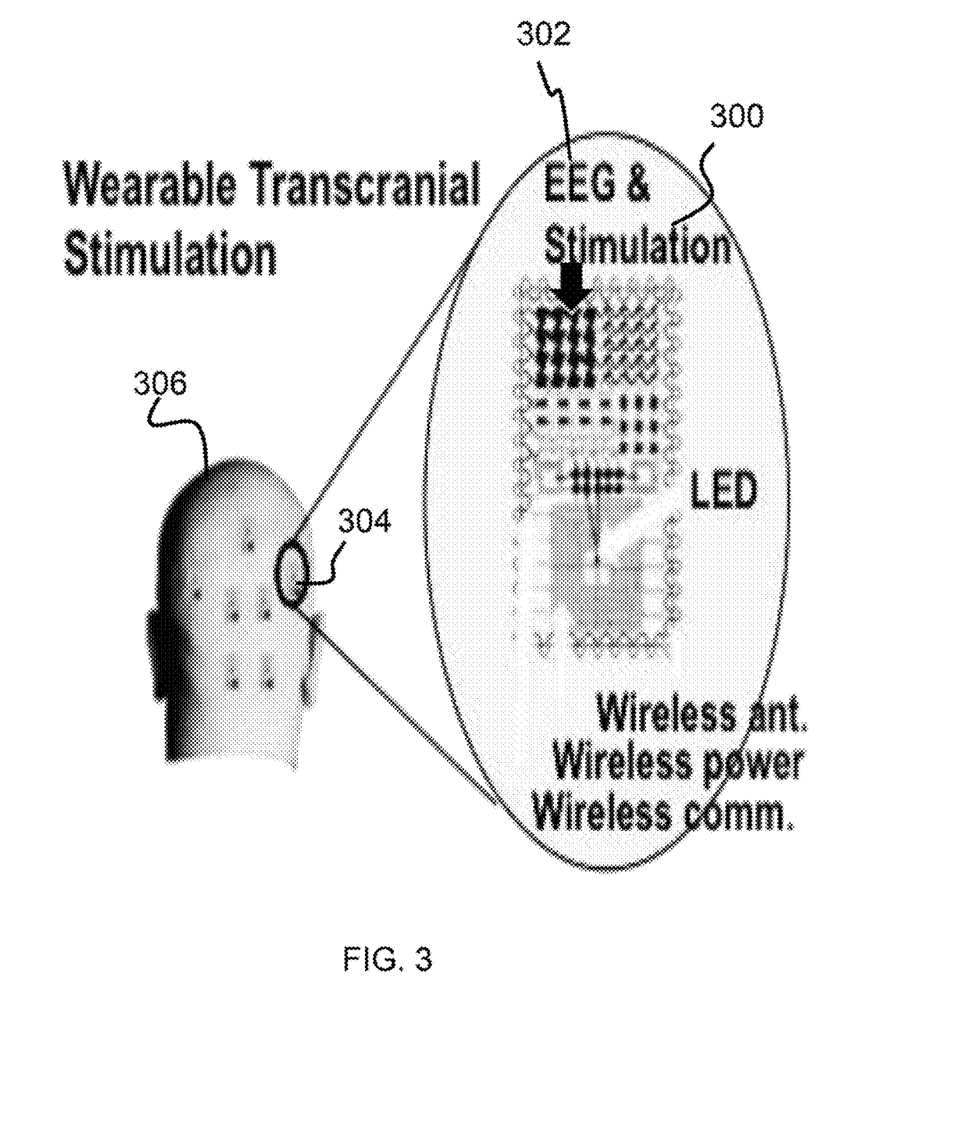
FIG. 3 is an illustration of an example wearable transcranial stimulation device that can be employed to provide transcranial stimulation according to some embodiments of this disclosure.

Further, the procedural memory enhancement system allows, for the first time, a targeted personalized closed-loop system (e.g., sensing and stimulation) for enhancing the learning of procedural skills. As a non-limiting example, a company known as MC-10 (located at 10 Maguire Road, Building 3, 1$^{st}$ Floor, Lexington, Mass. 02421) develops virtually invisible, conformal, and stretchable electronic sensors that adhere to the skin. The possibility of adding stimulation electrodes 300 to their current EEG sensors 302, as illustrated in FIG. 3, is a possibility that would greatly enhance the system of the present invention, by allowing for the creation of an active "tattoo" 304 on the head 306 that would both sense and adapt brain states.

For many reasons, the procedural memory enhancement system could be an enormous commercial success, due to at least the following advantages with specific details provided further below:

The procedure is safe; it does not require drugs

The system can be self-trained when the user is first learning a skill, or practicing it accurately The intervention can be either self-applied during wake, or automatically applied at night, and does not require supervision by a doctor or a psychological therapist The intervention is targeted; it is applied only during the wake reconsolidation period or the sleep consolidation of the skill memory (on the order of minutes) compared with a drug treatment whose effects can last for many hours and have unintended systemic chemical side-effects.

(4) Specific Details of Various Aspects

When a subject learns a skill, it is first encoded in the declarative memory system. Slowly, over time, the procedural system is trained. This training occurs partly through manual practice during waking states. However, a significant portion of the learning occurs during the sleep state: as the declarative memories are recalled spontaneously, the cortical procedural system is trained. The present invention addresses both phases of learning. As mentioned above, a procedural skill is first learned by the rapid declarative memory system. Whenever a procedural memory is recalled (i.e., a procedural skill is executed), for a short period of time it is labile and susceptible to modification. The approach of the present invention is to record brain activity during an initially rare trial when the subject performs a procedure perfectly under high levels of deliberative concentration. Subsequently, if the subject makes an error in practice of the skill during waking, this "practice pattern" can be recreated by using safe, low-level high-definition transcranial current stimulation, thereby interfering with reconsolidation of the bad performance. The present invention also allows the option to literally disrupt the reconsolidation process by targeting transcranial cathodal stimulation to cortical areas involved in procedural memory execution (e.g., primary motor area (M1), supplementary motor area). The method and apparatus of the present disclosure is described below, as well as how the stimulation parameters required to recreate the practice pattern are found. In addition, a method is presented to replay the practice pattern during sleep by automatically invoking the application of its temporally compressed version, to accelerate the conical consolidation of the procedural memory skills across the relevant neocortical areas.

Figure 4:
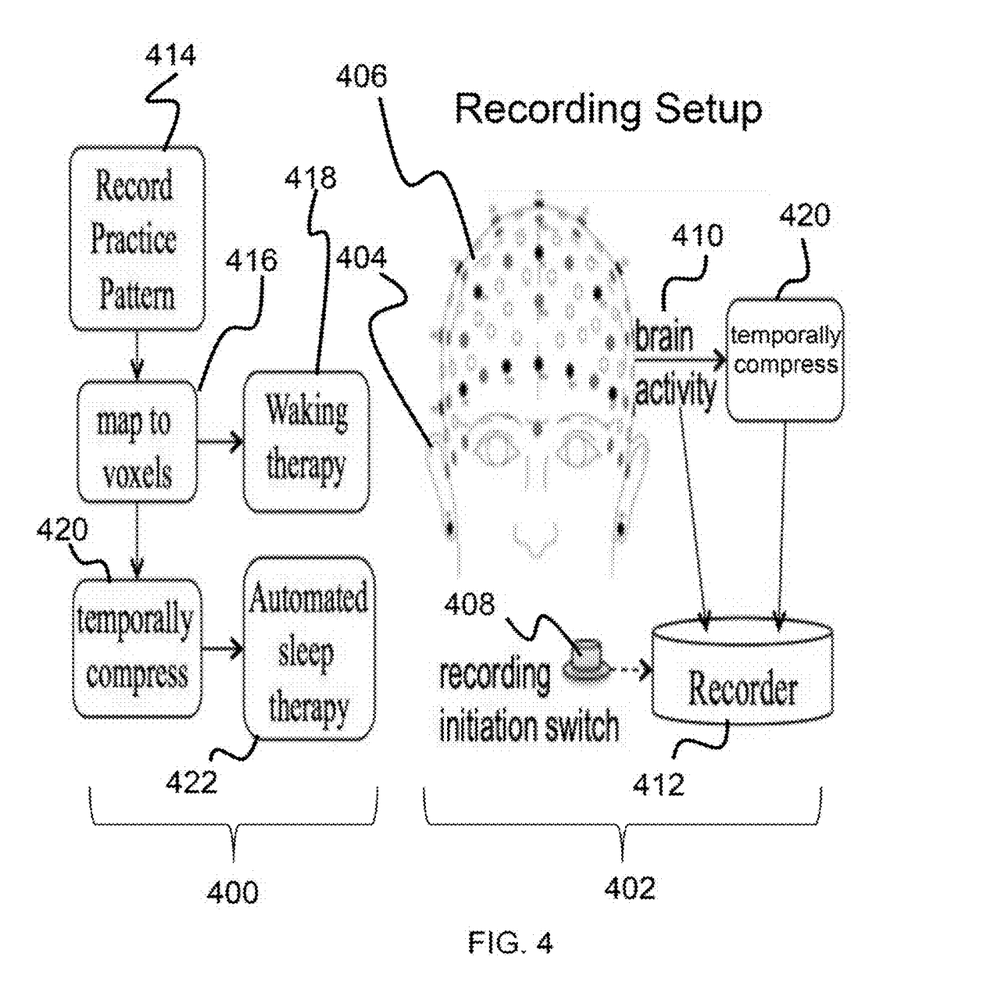
FIG. 4 is an illustration of system flow diagram, depicting ordering of procedures leading to two types of therapy coupled with a system architecture diagram for user-initiated recording of a practice signal according to some embodiments of this disclosure.

FIG. 4 presents a basic flow diagram 400 of the overall system and the architecture 402 to record patterns of brain activity, which is initiated by the subject 404. The subject 404 wears a sensor/stimulator array 406, which is a high-density array of sensors and stimulators worn on the head. The sensor/stimulator array 406 contains sensors such as EEG (electro-encephalogram) and fNIRS (functional near-infrared spectroscopy), and electrical stimulators such as HD-tCS (high-definition tCS). The sensor/stimulator array 406 can be formed in any suitable shape or manner so long as it is affixable with the subject 404 and capable of providing the functions described herein. For example, the sensor/stimulator array 406 can be an elastic headcap (as shown in FIG. 4), or engineered in a more ergonomic design, such as the wearable "tattoo" shown in FIG. 3.

As shown in FIG. 4, the subject 404 initiates 408 a recording (e.g., through a recording initiation switch or any other activation/initiation means) when learning or practicing the skill. Only the best performance should be used, so the subject might record multiple executions of the skill and only keep the best. Speed of execution is not as important as perfect performance, so the best recording might be a slow, deliberate performance under supervision of the expert that is training the skill. For example, when learning guitar, the student can often play a musical sequence slowly and perfectly with the guitar teacher and record it at that time. The subject or the trainer notifies the system (e.g., by button push as illustrated), initiating 408 a recording of brain activity 410 ("practice pattern") from the sensors (in the sensor/stimulator array 406) to a recording device 412 during the performance of the skill.

Figure 5A:
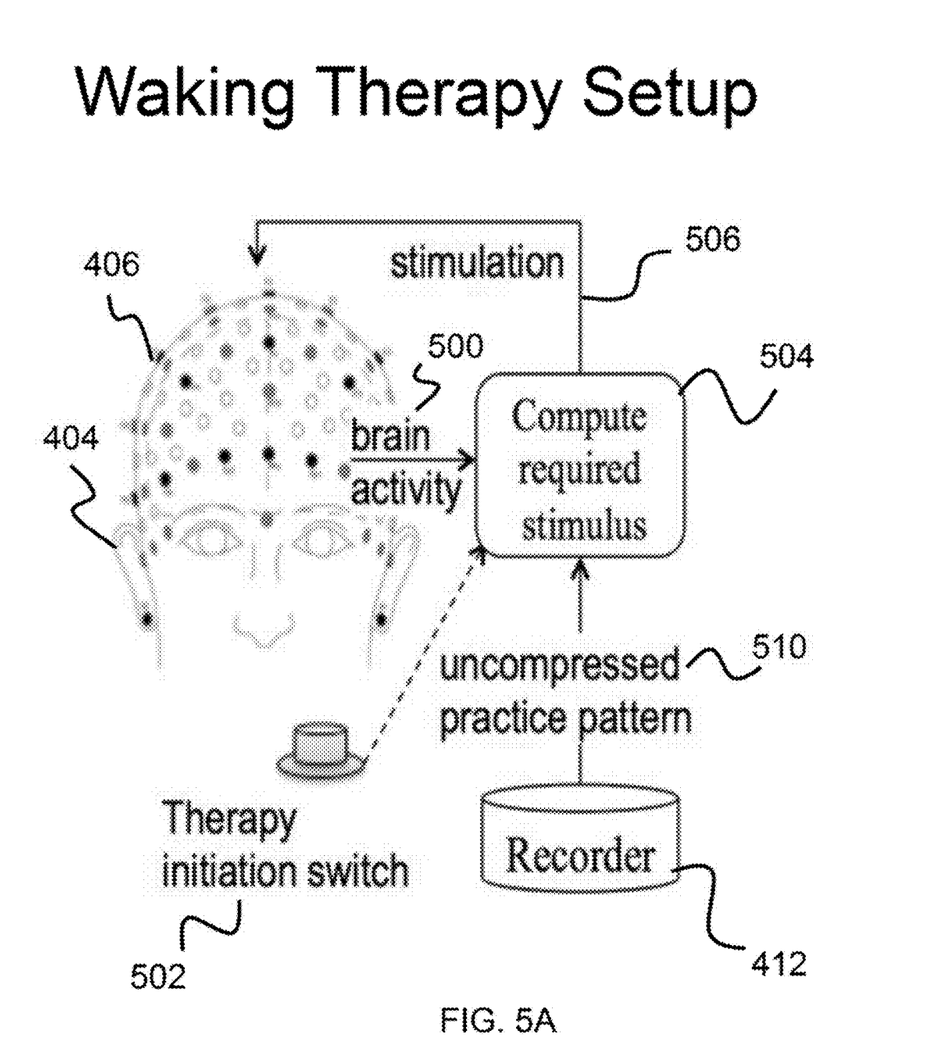
FIG. 5A is an illustration depicting user-initiated therapy during waking hours according to some embodiments of this disclosure.
Figure 5B:
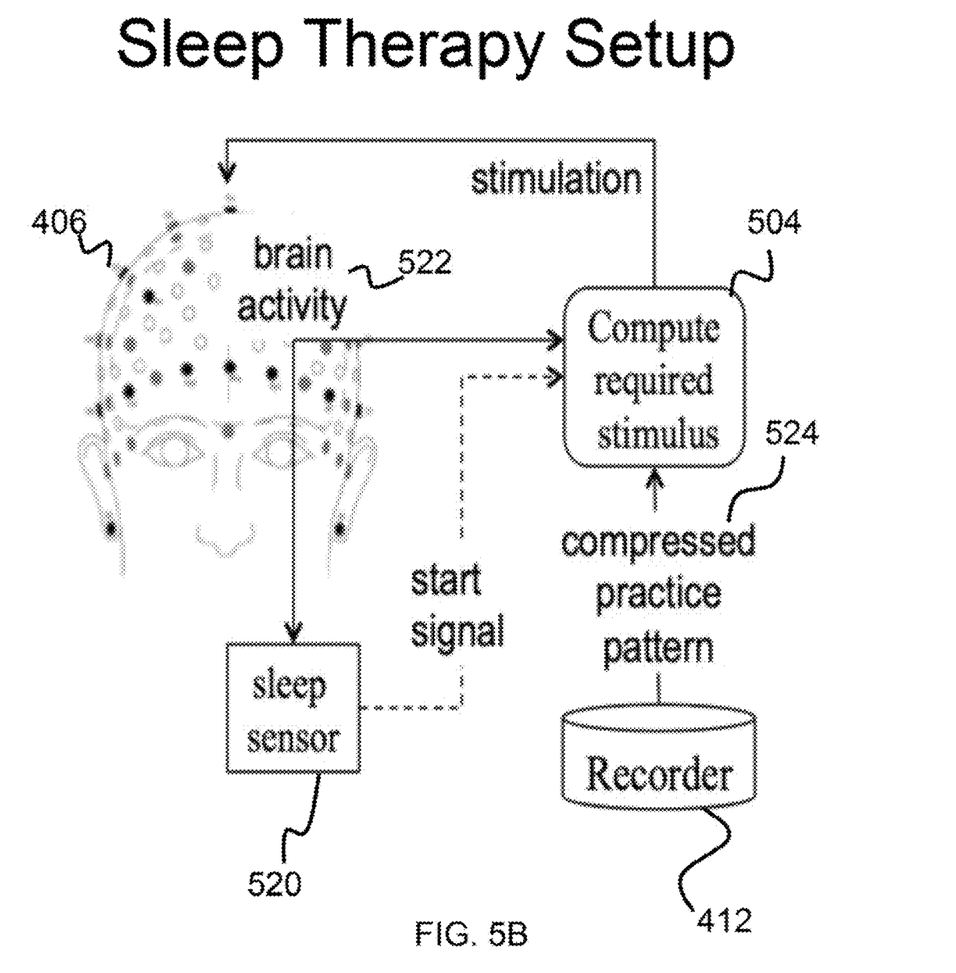
FIG. 5B is an illustration depicting therapy during sleep according to some embodiments of the present invention.

FIG. 5A illustrates how the waking neocortical brain activity 500 is converted into a temporally compressed form (using, for example, a generic compression factor of six to seven; see Literature Reference No. 3 for a description of temporal compression) to cue consolidation of the skill during sleep (shown in FIG. 5B). Cortical replay typically occurs at a faster rate than the waking experience; individual subjects may have different cortical replay rate (see Literature Reference Nos. 3 and 4), so the user or a trainer can adjust it (i.e., temporal compression) up or down to find the best match. The best setting for this parameter will be a subjective judgment of skill improvement when using the system overnight or over a number of nights; however, if there are metrics on the skill, the parameter setting can be objectively assessed.

As shown in FIG. 4, the recording 414 of the practice pattern (brain activity 410 signals obtained from the transcranial sensors (in the sensor/stimulator array 406)) must first be mapped 414 (converted) to voxels of activity in the brain prior to providing the therapy. Computing the neural activity in areas of the brain volume based on transcranial sensor data (EEG and/or fNIRS) is a problem known in the art as blind source separation, which discovers the most likely sources of the activity recorded from scalp electrodes. Then voxels with low activity are quenched (e.g., set voxels with less than 10% of the highest voxel activity to zero). The voxel activity (through voxel mapping 416) representing the practice pattern 414 (from the brain activity 410) is stored in the recorder 412 both in an uncompressed form (for waking therapy 418 as in FIG. 5A) as an uncompressed practice pattern and temporally compressed form (as a compressed practice pattern) through signal compression 420 (for sleep therapy 422 as in FIG. 5B). Note that element 400 is a flow diagram, with element 420 depicting the temporally compression process that temporally compresses the brain activity recorded in element 414. This compression process takes place in the temporal compression module 420 in the architecture diagram of element 402, where the temporal compression module 420 is again recording the brain activity.

As illustrated in FIG. 5A, after the practice pattern is recorded (in the recorder 412) in at least the uncompressed form, the system maps the recorded practice pattern to voxels 416 and also temporally compresses 420 the pattern. The system provides therapeutic stimulation by, for example, implementing a stimulation montage controller 504 that computes the required stimulus by comparing the current brain activity 500 with the recorded uncompressed practice pattern 510 to find the difference between current brain activity 500 and the correct practice-related brain activity. Based on the voxel mapping, the stimulate montage controller 504 finds a stimulation montage 506 that will reproduce the required activity pattern across the brain to minimize the difference between current brain activity 500 and the correct practice-related brain activity. The system then causes the stimulators (e.g., electrode stimulators) in the sensor/stimulator array 406 to provide the determined stimulation montage 506 to the subject 404. For example, say the subject practices a tennis serve to performance criterion (i.e., a tennis coach teaches the subject how to serve and the subject practices slowly and carefully, under supervision). In each practice trial, the subject initiates a recording (with switch 408) for the duration of the trial, until the coach observes a trial that is accurate. At that point, the system can be used during subsequent practice trials to make it more likely that the subject will execute the skill perfectly. The subject initiates the system before each practice trial, and the system reproduces the brain state from the accurate execution.

As shown in FIG. 5B, for procedural skill enhancement during sleep, the system of the present invention could use any of several types of sleep classifiers (i.e., sleep sensors 520) known to those skilled in the art to recognize deep sleep. A non-limiting example of such a sleep sensor 502 includes the FP-STAGER algorithm (see, for example, Literature Reference No. 5).

Periodically, during that sleep state, the recorded compressed practice pattern 524 (as stored in the recorder 412) can be used to cue recall of the skill during sleep. Here, the sleep sensor 520 detects when the subject is in NREM sleep, and then begins a period of stimulation using a montage that is simply the compressed pattern of EEG that was captured during accurate practice of the skill. This practice pattern should be applied during positive phases of some percentage of slow-wave oscillations (SWO), but if it is not possible to determine the SWO cycle frequency (which is not a constant), a reasonable approximation would be to simply apply the practice pattern repetitively during some portion of the entire period of slow-wave sleep. The portion would be determined by one skilled in the art. For example, the guideline should be that it should be long enough to get a beneficial behavioral effect (when tested the next day), but not so long that other memories do not get consolidated. As a non-limiting example, a desired implementation would be approximately 30% of the slow-wave sleep period.

In summary, described is a system to enhance acquisition of procedural memories by using transcranially-applied electrical stimulation to disrupt waking consolidation of bad habits and to promote consolidation of correctly executed procedural performances during sleep. During use, the user or trainer indicates when performance of the skill has begun, initiating a recording of the sensed brain activity from the sensors that is stored when the execution is satisfactory ("practice pattern"). The practice pattern is converted to the inferred brain activity voxels and stored in a raw, real-time form, and in a version that is compressed in time by a factor known in the art as cortical replay speedup. During waking, when practicing the skill poorly, the user can initiate therapy, and the system will apply the transcranial stimulation corresponding to the uncompressed practice pattern at the electrodes on his/her scalp, thereby interfering with reconsolidation and breaking the bad habit. Further, during waking, when practicing the skill poorly due to habitual interference, the use can initiate therapy, and the system will apply transcranial stimulation to neocortical areas, namely, primary motor cortex and supplementary motor area, either to proactively inhibit them or to desynchronize their functional interactions temporarily (on the order of minutes). Alternatively and periodically during sleep, the invention can initiate therapy automatically, applying the transcranial stimulation corresponding to the compressed practice pattern at the electrodes on his/her scalp, thereby cueing memories of comet performance of the skill and speeding up transfer from explicit declarative memory to implicit procedural memory.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A procedural memory enhancement system, the system comprising:
    one or more processors and a memory, the memory being a non-transitory computer-readable medium having executable instructions encoded thereon, such that upon execution of the instructions, the one or more processors perform operations of:
        upon initiation by a user, recording a practice pattern when a subject is performing a skill, the practice pattern being a recording of a sensed brain activity from a sensor array when the subject is performing the skill;
        converting the practice pattern to brain activity voxels and storing the brain activity voxels as both an uncompressed practice pattern and a compressed practice pattern; and
        transcranially applying a stimulus montage through a stimulator array to recreate at least one of the compressed practice pattern and uncompressed practice pattern, the stimulus montage being a spatiotemporal pattern of transcranial stimulation.

2. The system as set forth in claim 1, further comprising a stimulator array for applying a stimulus montage to a subject.

3. The system as set forth in claim 2, wherein in recording the practice pattern, the practice pattern is recorded when the skill is performed correctly.

4. The system as set forth in claim 3, further comprising operations of:
    while a subject is awake and practicing the skill, determining a required stimulus montage that maximizes a difference between the uncompressed practice pattern and a current brain activity; and
    transcranially applying the stimulus montage to a subject through the stimulator array during subsequent waking practice of the skill.

5. The system as set forth in claim 4, further comprising an operation of:
    while a subject is awake and incorrectly practicing the skill, transcranially applying a stimulus montage corresponding to the uncompressed practice pattern to interfere with reconsolidation and break bad habits.

6. The system as set forth in claim 5, further comprising operations of:
    periodically while a subject is asleep, transcranially applying the compressed practice pattern as a stimulus montage to the subject through the stimulator array, thereby cueing memories of performance of the skill.

7. The system as set forth in claim 6, wherein responsive to user input, adjusting a compression level used to form the compressed practice pattern to adapt sleep training to the subject and thereby increase individual sleep training effectiveness.

8. The system as set forth in claim 1, wherein in recording the practice pattern, the practice pattern is recorded when the skill is performed correctly.

9. The system as set forth in claim 1, further comprising operations of:
    while a subject is awake and practicing the skill, determining a required stimulus montage that maximizes a difference between the uncompressed practice pattern and a current brain activity; and
    transcranially applying the stimulus montage to a subject through a stimulator array during subsequent waking practice of the skill.

10. The system as set forth in claim 1, further comprising an operation of:
    while a subject is awake and incorrectly practicing the skill, transcranially applying a stimulus montage corresponding to the uncompressed practice pattern to interfere with reconsolidation and break bad habits.

11. The system as set forth in claim 1, further comprising operations of:
    periodically while a subject is asleep, transcranially applying the compressed practice pattern as a stimulus montage to the subject through a stimulator array, thereby cueing memories of performance of the skill.

12. The system as set forth in claim 1, wherein responsive to user input, adjusting a compression level used to form the compressed practice pattern to adapt sleep training to the subject and thereby increase individual sleep training effectiveness.

13. A computer program product for procedural memory enhancement, the computer program product comprising:
    a non-transitory computer-readable medium having executable instructions encoded thereon, such that upon execution of the instructions by one or more processors, the one or more processors perform operations of:
        upon initiation by a user, recording a practice pattern when a subject is performing a skill, the practice pattern being a recording of a sensed brain activity from a sensor array when the subject is performing the skill;
        converting the practice pattern to brain activity voxels and storing the brain activity voxels as both an uncompressed practice pattern and a compressed practice pattern; and
        transcranially applying a stimulus montage through a stimulator array to recreate at least one of the compressed practice pattern and uncompressed practice pattern, the stimulus montage being a spatiotemporal pattern of transcranial stimulation.

14. The computer program product as set forth in claim 13, wherein in recording the practice pattern, the practice pattern is recorded when the skill is performed correctly.

15. The computer program product as set forth in claim 13, further comprising instructions for causing the one or more processors to perform operations of:
    while a subject is awake and practicing the skill, determining a required stimulus montage that maximizes a difference between the uncompressed practice pattern and a current brain activity; and
    transcranially applying the stimulus montage to a subject through a stimulator array during subsequent waking practice of the skill.

16. The computer program product as set forth in claim 13, further comprising instructions for causing the one or more processors to perform operations of:

while a subject is awake and incorrectly practicing the skill, transcranially applying a stimulus montage corresponding to the uncompressed practice pattern to interfere with reconsolidation and break bad habits.

17. The computer program product as set forth in claim 13, further comprising instructions for causing the one or more processors to perform operations of:
periodically while a subject is asleep, transcranially applying the compressed practice pattern as a stimulus montage to the subject through a stimulator array, thereby cueing memories of performance of the skill.

18. The computer program product as set forth in claim 13, further comprising instructions for causing the one or more processors to perform operations of:
wherein responsive to user input, adjusting a compression level used to form the compressed practice pattern to adapt sleep training to the subject and thereby increase individual sleep training effectiveness.

19. A method for procedural memory enhancement, the method comprising an act of:
causing one or more processors to execute instructions encoded on a non-transitory computer-readable medium, such that upon execution, the one or more processors perform operations of:
upon initiation by a user, recording a practice pattern when a subject is performing a skill, the practice pattern being a recording of a sensed brain activity from a sensor array when the subject is performing the skill;
converting the practice pattern to brain activity voxels and storing the brain activity voxels as both an uncompressed practice pattern and a compressed practice pattern; and
transcranially applying a stimulus montage through a stimulator array to recreate at least one of the compressed practice pattern and uncompressed practice pattern, the stimulus montage being a spatiotemporal pattern of transcranial stimulation.

20. The method as set forth in claim 19, wherein in recording the practice pattern, the practice pattern is recorded when the skill is performed correctly.

21. The method as set forth in claim 19, further comprising operations of:
while a subject is awake and practicing the skill, determining a required stimulus montage that maximizes a difference between the uncompressed practice pattern and a current brain activity; and
transcranially applying the stimulus montage to a subject through a stimulator array during subsequent waking practice of the skill.

22. The method as set forth in claim 19, further comprising an operation of:
while a subject is awake and incorrectly practicing the skill, transcranially applying a stimulus montage corresponding to the uncompressed practice pattern to interfere with reconsolidation and break bad habits.

23. The method as set forth in claim 19, further comprising operations of:
periodically while a subject is asleep, transcranially applying the compressed practice pattern as a stimulus montage to the subject through a stimulator array, thereby cueing memories of performance or the skill.

24. The method as set forth in claim 19, wherein responsive to user input, adjusting a compression level used to form the compressed practice pattern to adapt sleep training to the subject and thereby increase individual sleep training effectiveness.

* * * * *